(12) United States Patent
Krause

(10) Patent No.: US 12,161,370 B2
(45) Date of Patent: Dec. 10, 2024

(54) FLEXIBLE CONNECTING ROD FOR INDUSTRIAL APPLICATIONS

(71) Applicant: William R. Krause, Charlottesville, VA (US)

(72) Inventor: William R. Krause, Charlottesville, VA (US)

( * ) Notice: Subject to any disclaimer, the term of this patent is extended or adjusted under 35 U.S.C. 154(b) by 1012 days.

(21) Appl. No.: 17/142,115

(22) Filed: Jan. 5, 2021

(65) Prior Publication Data

US 2021/0121212 A1  Apr. 29, 2021

Related U.S. Application Data

(63) Continuation-in-part of application No. 16/155,362, filed on Oct. 9, 2018, now Pat. No. 10,883,532, which is a continuation-in-part of application No. 15/445,168, filed on Feb. 28, 2017, now abandoned, which is a continuation of application No. 13/830,379, filed on Mar. 14, 2013, now Pat. No. 9,579,132.

(51) Int. Cl.
*A61B 17/72* (2006.01)
*A61B 17/86* (2006.01)

(52) U.S. Cl.
CPC ...... *A61B 17/7233* (2013.01); *A61B 17/7208* (2013.01); *A61B 17/8605* (2013.01); *A61B 17/8625* (2013.01); *A61B 17/864* (2013.01); *A61B 17/866* (2013.01); *A61B 17/869* (2013.01)

(58) Field of Classification Search
CPC . A61B 17/72; A61B 17/7208; A61B 17/7216; A61B 17/7225; A61B 17/7233; A61B 17/7241; A61B 17/725; A61B 17/7258; A61B 17/7266; A61B 17/7275; A61B 17/7283; A61B 17/7291
See application file for complete search history.

(56) References Cited

U.S. PATENT DOCUMENTS

| | | |
|---|---|---|
| 5,643,258 A | 7/1997 | Robioneck et al. |
| 6,053,922 A * | 4/2000 | Krause ............... A61B 17/164 606/180 |
| 6,322,591 B1 | 11/2001 | Ahrens |
| 6,503,249 B1 | 1/2003 | Krause et al. |
| 8,130,879 B2 | 3/2012 | Huang |
| 9,060,809 B2 | 6/2015 | Tipimeni et al. |
| 2005/0277936 A1 | 12/2005 | Siravo et al. |
| 2007/0173834 A1 | 7/2007 | Thakkar |
| 2008/0183170 A1 | 7/2008 | Metzinger et al. |
| 2008/0057868 A1 | 9/2008 | Stoneburner et al. |

(Continued)

FOREIGN PATENT DOCUMENTS

RU   2334580   9/2008

*Primary Examiner* — Si Ming Ku
(74) *Attorney, Agent, or Firm* — Kimberly O Snead

(57) ABSTRACT

A flexible connecting system consists of a flexible connecting rod manufactured from a rigid material, a leading segment and a trailing segment. The body has at least one flexible center section, each having at least one slot to provide flexibility. The slot follows a sinuous, serpentine path to form a plurality of interlocking teeth that can follow a helical or a concentric path. One or more flexible sleeves are dimensioned to fit over the connecting rod to prevent the ingress or egress of material. One or both of the ends of the flexible connecting rod and flexible sleeve can be open or sealed.

20 Claims, 9 Drawing Sheets

(56) References Cited

U.S. PATENT DOCUMENTS

| | | |
|---|---|---|
| 2009/0177240 A1 | 7/2009 | Perez |
| 2010/0134078 A1 | 6/2010 | Murakami et al. |
| 2011/0144703 A1* | 6/2011 | Krause ................ A61B 17/869 |
| | | 606/309 |

* cited by examiner

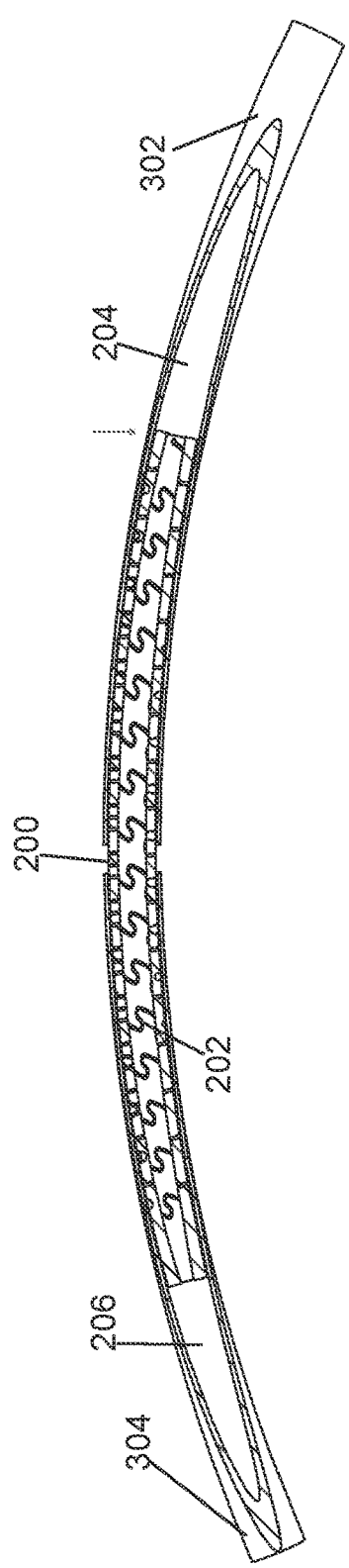
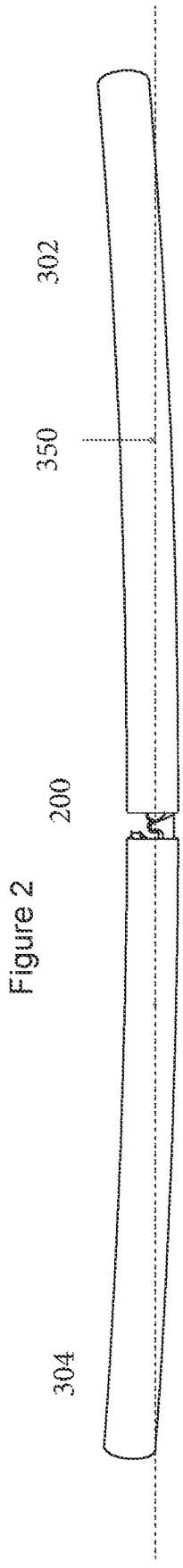
Figure 2
Figure 3

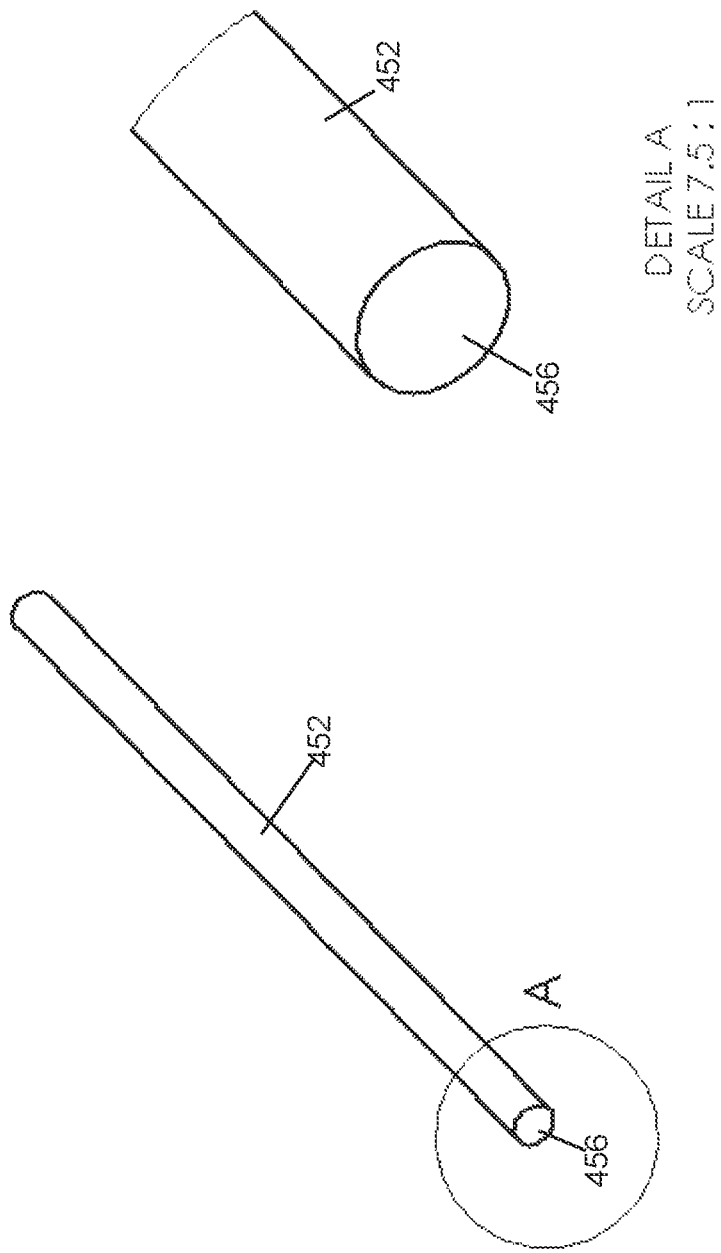

FLEXIBLE CONNECTING ROD FOR INDUSTRIAL APPLICATIONS

FIELD OF THE INVENTION

The present invention relates generally to the repair and connection of flexible tubing and semi-flexible structures using an internal flexible splint.

BACKGROUND OF THE INVENTION

The application of flexible fastening devices encompasses a broad spectrum of industries, included, but not limited to, manufacturing, construction, mining, transportation, agriculture, aviation, automotive, and medical. Flexible fastening devices, either tapered like screws or flat end like bolts, have the characteristics in which the cylindrical portion of the device is bendable about the longitudinal length. Flexible fastening devices are useable in many applications, from manufacturing to medical, to secure to objects together.

In U.S. Pat. No. 3,627,354 a flexible connector is disclosed that comprises a tubular member having a central corrugated portion and having an un-corrugated end portion with braided strings to provide a mechanical friction connection. This, however, provides a complicated and costly device.

The connection of two or more flexible structures or semi flexible structures is a challenge, especially when the entry points are not in alignment. This is exemplified in the connection of metallic, plastic, and rubber tubing, in addition to the repair of biological materials such as blood vessels and bones. Additionally, support of flexible structures in a flexed configuration can be difficult in that to maintain the curved configuration, the material must have more rigidity than would be advantageous in the remaining application.

The connection of two structures, such as tubing, is further complicated when the connecting device needs to accommodate fluid transfer. In such cases, the serpentine slot is filled with a polymer or the entire shaft is encapsulated in a polymer.

The present invention overcomes the deficiencies and problems evident in the prior art as described herein above by combining the following features into an integral, longitudinally, laterally and torsionally flexible segment of the component.

SUMMARY OF THE INVENTION

A flexible connecting system for connection of two structures having a flexible connection rod and at least one flexible sleeve. The flexible connecting rod having a substantially cylindrical hollow body with a leading segment and a trailing segment, and at least one slot following a sinuous, serpentine path to form a plurality of interlocking teeth to provide flexibility. The at least one slot can follow a helical path along a portion of the body, consist of multiple concentric slots, or be a combination of the two. The flexible sleeve having a proximal end, distal end, exterior, and hollow interior for receiving the flexible connection rod such that the flexible sleeve prevents passage of material between the hollow core of the connection rod and the exterior of the sleeve.

In the connection system a connection rod can be inserted into one or more flexible sleeves. If one flexible sleeve is used, the leading segment is inserted into the open distal end of the flexible sleeve. The proximal end of the flexible sleeve can be open or closed. If two flexible sleeves are used in the connection system, the leading segment is inserted into the open distal end of one flexible sleeve while the trailing segment is inserted into the open distal end of a second flexible sleeve. The proximal ends of the two flexible sleeves can be open or closed. With either of the one or two sleeve configurations, the hollow flexible connection rod can have either open or closed ends in the leading and trailing segments. At least one of the flexible rod ends must be open if fluid flow into the flexible rod core is desired. Both ends of the flexible rod must be open if fluid flow completely through the rod core is desired.

Each of the at least one slot has a proximal end and a distal end, with the proximal end being spaced from the trailing segment and the distal end being spaced from the leading segment. When multiple slots are used the proximal and distal ends of each slot can be spaced from one another or adjacent thereto, Each slot can have a varied flexibility and/or pattern in relationship to other slots, with increased or decreased flexibility with respect to other slots. The multiple slots can be separated by a non-slotted section.

Each of the slots can have sufficient width to form an unbound joint permitting limited movement in any direction upon application of tensile, compressive, and/or torsion forces. Each of the slots can also have an increased width in a first direction compared to a second direction to provide increased flexibility in the first direction.

The varied flexibility is achieved by varying the pitch of the helical slot and helix angle, with the helical angle being in the range of about 5 degrees to about 45 degrees, and/or the amplitude and frequency of the slot cycle. The varied flexibility can also be achieved by varying the width of the helical slot, instead of or in addition to the helical angle, amplitude, and frequency of the slot cycle. The slot width is between about 0.5% and about 15.0% of the diameter of flexible rod with a maximum of 20% to 25%.

The ratio of the amplitude of the path to the pitch of the slot is in the range from greater than 0.1 to about 0.8. The helical path of one or more slots is about 0.25 to about 5 cycles per diameter length and the helical angle ranges from about 5 degrees to about 45 degrees.

The disclosed flexible connecting rod is manufactured from a rigid material appropriate for end use and has a substantially cylindrical hollow body. The body has at least one flexible center section, each having at least one slot to provide flexibility. In one embodiment the slot follows a sinuous, serpentine path to form a plurality of interlocking teeth. The flexibility can be obtained from the slot or slots following a helical path or a concentric path. The helical path of the slot(s) is about 0.25 to about 5 cycles per diameter length and the helical angle ranges from about 5 degrees to about 45 degrees. The ratio of the amplitude of the path to the pitch of the slot is in the range from greater than 0.1 to about 0.8. The width of each slot between about 0.5% and about 5.0% of the diameter of said flexible rod. Each of the slots following a helical path has a proximal end and a distal end, with the proximal end being spaced from the trailing segment and the distal end being spaced from the leading segment. When multiple slots are incorporated, the proximal end of a slot is spaced from a distal end of a subsequent slot. The first of the at least one flexible center section and a second of the at least one flexible center section can be separated by a non-slotted section. When the sinuous slots follow a circumferential path, multiple slots encircle the flexible connecting rod spaced a predetermine distance from one another.

Each of the at least one slot can have a varied flexibility in relationship to another of slot from the group comprising increased flexibility, decreased flexibility, equal flexibility. Each of the slots can have sufficient width to form an unbound joint permitting limited movement in any direction upon application of tensile, compressive, and/or torsion forces. Alternatively, each slot can have an increased width in a first direction compared to a second direction to provide increased flexibility in said first direction. The varied flexibility can be achieved by varying the pitch of the helical slot and helix angle, said helical angle being in the range of about 10 degrees to about 45 degrees. The flexibility can also be achieved by varying the width of the helical slot.

Advantageously, the slot is cut at an angle normal to the shaft using a computer controlled cutting technique such as laser cutting, water jet cutting, milling or other means. Additionally, this slot may be cut at an angle to the normal so as to provide an undercut slot; preferably the angle is in the range from about 5 to about 45 degrees from the normal.

The sinusoidal wave forms dovetail-like teeth, which have a narrow base region and an anterior region which is wider than the base region. Thus, adjacent teeth interlock. The teeth can have a configuration as illustrated in U.S. Pat. No. 4,328,839, the disclosure of which is incorporated herein by reference, as though recited in detail.

An important aspect of this invention therefore lies in providing a rod for insertion in, and connection of, nonlinear structures. An additional aspect is a mechanism that causes the flexible rod to become rigid to provide additional support to all or a portion of the structure being connected.

BRIEF DESCRIPTION OF THE DRAWINGS

Examples of the invention are illustrated in the drawings herewith. All of the figures are drawn on an undersized scale, and like structure in different figures bears like reference numerals.

FIG. 2 is a view of a slightly flexed flexible rod within the flexible tubing of FIG. 2 in accordance with the present invention;

FIG. 3 is a cutaway of a flexible connecting rod in accordance with the present invention;

FIG. 11 is an isometric view of a flexible connecting rod having a closed end in accordance with the invention; and FIG. 12 is a detailed end view of the flexible connecting rod of FIG. 11.

DESCRIPTION OF THE PREFERRED EMBODIMENTS

Figure 1:
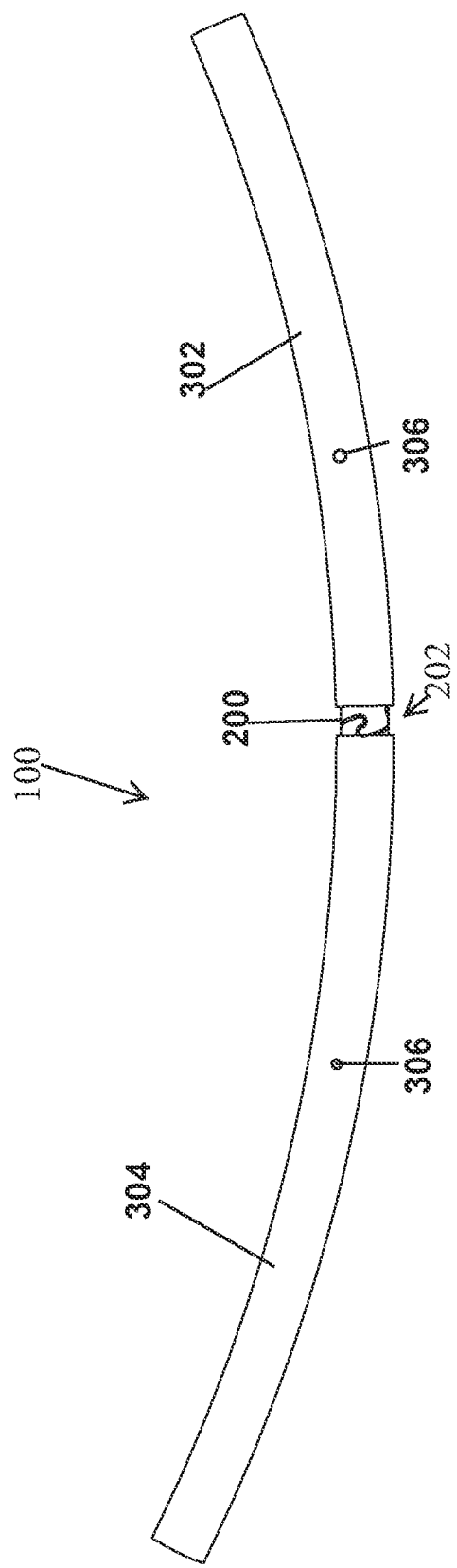
FIG. 1 illustrates the flexible connecting rod connecting two pieces of flexible tubing in accordance with the present invention.

For the purposes herein the term "flexible connecting rod", refers to a hollow, metal rod that connects two flexible or semi-flexible structures.

For the purposes herein the terms "slit", and "slot" are used interchangeably, consistent with their definitions, as follows:
  a. slot n. 1. A narrow opening; a groove or slit: a slot for coins in a vending machine; a mail slot.
  b. 2. A gap between a main and an auxiliary airfoil to provide space for airflow and facilitate the smooth passage of air over the wing.

For the purposes herein the term pitch as used herein is defined as:
  a. pitch-n.1. The distance traveled by a machine screw in one revolution.
  b. The distance between two corresponding points on adjacent screw threads or gear teeth. (American Heritage Dictionary, 3rd. Edition, Copyright 1994)

For the purposes herein the term "cycle" shall refer to:
  a. Cycle-1. An interval of time during which a characteristic, often regularly repeated event or sequence of events occurs: Sunspots increase and decrease in intensity in an 11-year cycle.
  b. 2.a. A single complete execution of a periodically repeated phenomenon: A year constitutes a cycle of the seasons.
  c. 2b. A periodically repeated sequence of events: cycle includes two halves of the sinewave like undulation of the slot path. (American Heritage Dictionary, 3rd Edition, Copyright 1994)

For the purposes herein the term "amplitude" shall refer to the maximum absolute value of the periodically varying quantity of the slot.

For the purposes herein the term "serpentine" shall refer to:
  a. 3 a: winding or turning one way and another <a serpentine road>
  b. b: having a compound curve whose central curve is convex. (Merriam-Webster online dictionary)

For the purposes herein the "sinuous" shall refer to:
  a. a: of a serpentine or wavy form: winding,
  b. b: marked by strong lithe movements. (Merriam-Webster online dictionary)

For the purposes herein the term "serpentine" and "sinuous" are interchangeable and shall refer to a winding or turning one way and then another to not follow a straight line, except for brief instances.

For the purposes herein the terms "segment" and "section" are interchangeable and shall refer to slotted and unslotted areas of the flexible rod, dimensioned to meet end use requirements.

For the purposes herein the term "helical", "helix" and "spiral" are interchangeable and shall refer to:
  a. 1 a: winding around a center or pole and gradually receding from or approaching it <the spiral curve of a watch spring> b: helical c: spiral-bound <a spiral notebook>
  2 of or relating to the advancement to higher levels through a series of cyclical movements. (Merriam-Webster online dictionary)

For the purposes herein the term "frequency" shall refer to the number of times a specified phenomenon occurs within a specified interval:
   a. Frequency.
   b. 1 a. Number of repetitions of a complete sequence of values of a periodic function per unit variation of an independent variable.
   c. 1b. Number of complete cycles of a periodic process occurring per unit time.
   d. 1c.: Number of repetitions per unit time of a complete waveform, as of an electric current. The number of times the cycles form a repetitive pattern in one unit of length is the frequency of the slot pattern. The number of cycles "C" of the slot undulations superimposed upon the circumferential path which are present in one revolution around the shaft, is referred to as the cycles per revolution. (American Heritage Dictionary, 3rd Edition, Copyright 1994)

For the purposes herein the term "sleeve" and "tubing" are interchangeable and shall refer to a flexible tubular covering dimensioned to receive the disclosed flexible connecting rod.

While the present invention will be described more fully hereinafter with reference to the accompanying drawings, in which particular embodiments and methods of implantation are shown, it is to be understood at the outset that persons skilled in the art can modify the invention herein described while achieving the functions and results of this invention.

Flexible connecting fixation devices are useable in many applications from securing rubber seal strips, to connecting flexible fluid tubes, to providing fracture fixation to a number of different bones. Accordingly, the descriptions that follow are to be understood as illustrative and exemplary of specific structures, aspects, and features within the broad scope of the present invention and not as limiting of such broad scope.

The invention relates to a flexible connecting system comprising a flexible connecting rod and at least one flexible sleeve dimensioned to fit over the flexible connecting rod. The connecting rod has one or more flexible segments within the center area of the rod, although in some embodiments, depending on end use, the flexible segments can extend to the end of the rod. When containing multiple flexible segments, these segments can be separated by a solid section to position the flexibility of the rod along its length. The flexibility can be created through the use of at least one sinuous helical slot, or multiple concentric slots.

The flexible tubing of the present invention can include one or more flexible sleeves and covers at least a portion of the connection rod and can cover the entirety of the connection rod depending on the end use of the connection system. Regardless of the sleeve configuration, the connection system of the present invention provides that at least one end of the connection rod is inserted into a flexible sleeve and the sleeve is manipulated around the connection rod until in the desired location along the connection rod. The flexible sleeve is secured in place along the connection rod by a preferred securing means which includes but is not limited to a securing mechanism such as a crimp or pin, adhesive, or friction. The securing means used will depend on the end use of the system and the preference of those skilled in the art. Once the flexible sleeve is secured in place, the connection system is ready for implantation into connectable structures. Once implanted into the structures, an open ended connection system allows for fluids to be introduced into the connection rod and maintained within or passed through the connection system without leakage.

In other embodiments, additional flexible segments also have at least one sinuous helical slot in either the same helical rotation and pattern or in an opposite rotation and/or different pattern. In another embodiment the flexible section or sections has a flexible segment that has at least one helical, sinuous slot within a section of the element that is embedded within a polymer or other flexible material so as to encapsulate the rod and fill the slot with the flexible material as disclosed in U.S. Pat. Nos. 6,053,922, 6,447,518 and 10,883,532 which are incorporated herein as though recited in full.

In applications where the disclosed flexible connecting rod is used to connect flexible or semi-flexible structures and additional stability is required after implantation of flexible connecting rod, the appropriate cement or other materials can be injected in the entry holes. The slotted flexible section of the rod provides a flow-through mechanism for cement that is used for production of a cement jacket around the rod, such that rod will be anchored in a highly stable manner after being implanted. This is especially advantageous when the flexible connecting rod is being used as a replacement for a dowel.

The disclosed flexible connecting rod can also be used to provide support in critical areas as well as, when combined with the disclosed locking shaft, to maintain a flexible structure in a user determined curve.

In addition to connect ng two flexible structures, the disclosed flexible connecting rod can be used to connect two structures that are in nonlinear alignment. This use can be applicable to furniture or bones and would incorporate a smaller flexible section with longer inflexible proximal and distal ends.

The use of the flexible tubing, or sleeve, to cover the connecting rod prevents external material from entering the slot or material being maintained within the connecting rod from exiting through the slot. An encapsulated system is provided to prevent the transfer of materials into and out of the flexible connecting system. For example, in medical usage, the sleeves prevent tissue growth into the flexible connecting rod.

Additionally, the use of the connecting system can permit removal of the rod and separation of the structures being secured. The adhesion of the sleeve into the structures to be connected and then subsequent addition, and removable securing, of the flexible connecting rod enables the rod to be removed from the structure. This is particularly useful in situations as described above where additional stability is required after implantation of the connection rod. In such a situation, the cement added for stability is enclosed within the sleeve thus preventing the cement from permanently adhering to the interior of the structures being secured. Accordingly, stability is provided while allowing for the potential future removal of the rod.

The flexible connecting system can also be used to connect two structures where flexible separation is desired. By covering the flexible connecting rod with the sleeve, the exposed portion of the rod will not cause injury.

FIG. 1 is a diagrammatic illustration of the assembled flexible connecting system 100 consisting of the connecting rod 200 positioned within two flexible tubing sections, or sleeve 302 and sleeve 304. In the illustrated example each end is accessible for securing with a securing member 306, such as crimp or a pin. Alternatively, adhesive can be added to the interior of the sleeve 302 and sleeve 304, or the rod 200, thereby securing the rod 200 within the sleeve 302 and sleeve 304. In some embodiments, such as when the assembled unit 100 is being compressed by the material within which it lies, the sleeve 302 and sleeve 304 can be maintained on the rod 200 by friction. The nature of securing the sleeve 302 and sleeve 304 to the rod 200 will be dependent upon the material being connected and end use and will be known to those skilled in the art. While FIG. 1 shows an embodiment having two sleeves, a connection system could utilize one sleeve or more than two sleeves. The number of sleeves used on any particular connecting rod will be dependent upon end use and preference and known to those skilled in the art.

In the example of FIG. 1, there is a gap 202 between sleeve 302 and sleeve 304. The gap 202 is optional and incorporation of the gap in the assembled connection unit 100 is dependent upon preference and end use.

In FIG. 2 the flexible connecting rod 200 is shown inserted in the flexible tubes 302 and 304 with the slight flex from the normal plane indicated by line 350.

FIG. 3 illustrates a cutaway of the flexible connecting rod system 100 with the flexible connecting rod 200, using a single slot 202 in a helical path. Although untapered, the ends of the flexible connecting rod 200 can have a slight taper as disclosed hereinafter. Additionally, the ends of the connecting rod 200 can be open or closed as disclosed herein.

Figure 4:
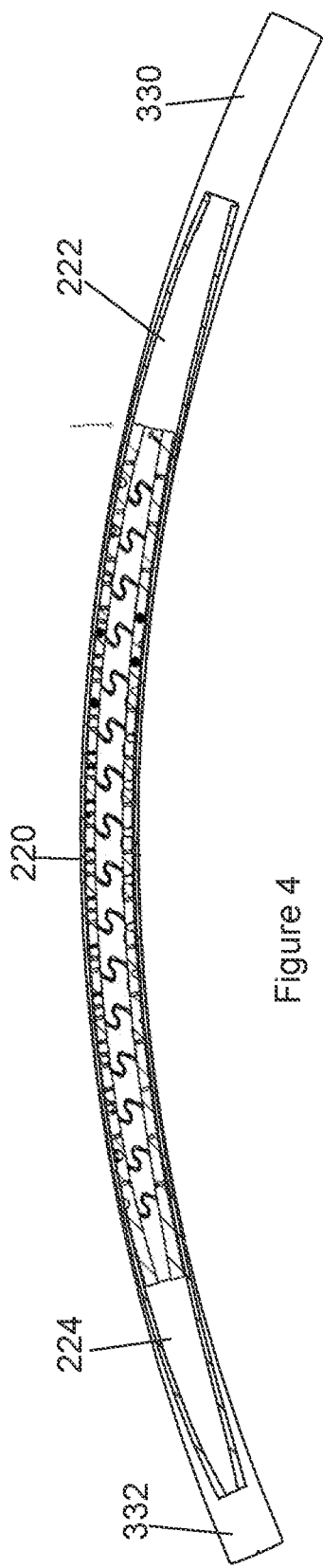
FIG. 4 is a cutaway of a flexible connecting rod allowing fluid flow in accordance with the present invention.

In applications where fluid transfer within the flexible structure being connected is of concern, the embodiment of FIG. 4 is incorporated. The flexible connecting rod 220 has an open distal end 224 and open proximal end 222 to enable fluid to flow through the rod 220, sleeve 330 and sleeve 332. To prevent fluid leakage the flexible tubing 330 and 332 should abut one another and the securing member maintained in place with an adhesive. An elastomeric coating can also be applied in addition to the sleeve 330 and sleeve 332 to ensure the prevention of fluid leakage. In this embodiment the distal end 224 and proximal end 222 have a reduced diameter to permit easier insertion of the tube 322 into sleeve 330 and sleeve 332. As stated herein, the need for diameter reduction as well as the degree of reduction will depend upon end use and will be evident to those skilled in the art.

In industrial applications, the slot width would be between about 0.5% and about 15.0% of the diameter of the connecting rod, with a maximum of about 20% to 25%. For a given diameter, the higher the percentage slot width, the flexible the shaft will be more flexible.

In applications where smaller dimensions are required, such as delicate furniture, clock repair, medical, etc., the helical path of the slot 128 is about 0.25 to about 5 cycles per diameter length. In order to provide the desired flexibility, while maintaining support, the width of the slot 128 should not exceed about 0.075 of an inch in a rod or shaft having a diameter in the range from about 0.10 to about 0.750 inches, with a general width of about 0.005 to about 0.050 inches. Alternatively, the width to diameter percentages can be between about 0.5% and about 5.0% of the diameter of the element. The helical angle ranges from about 5 degrees to about 45 degrees.

Figure 5:
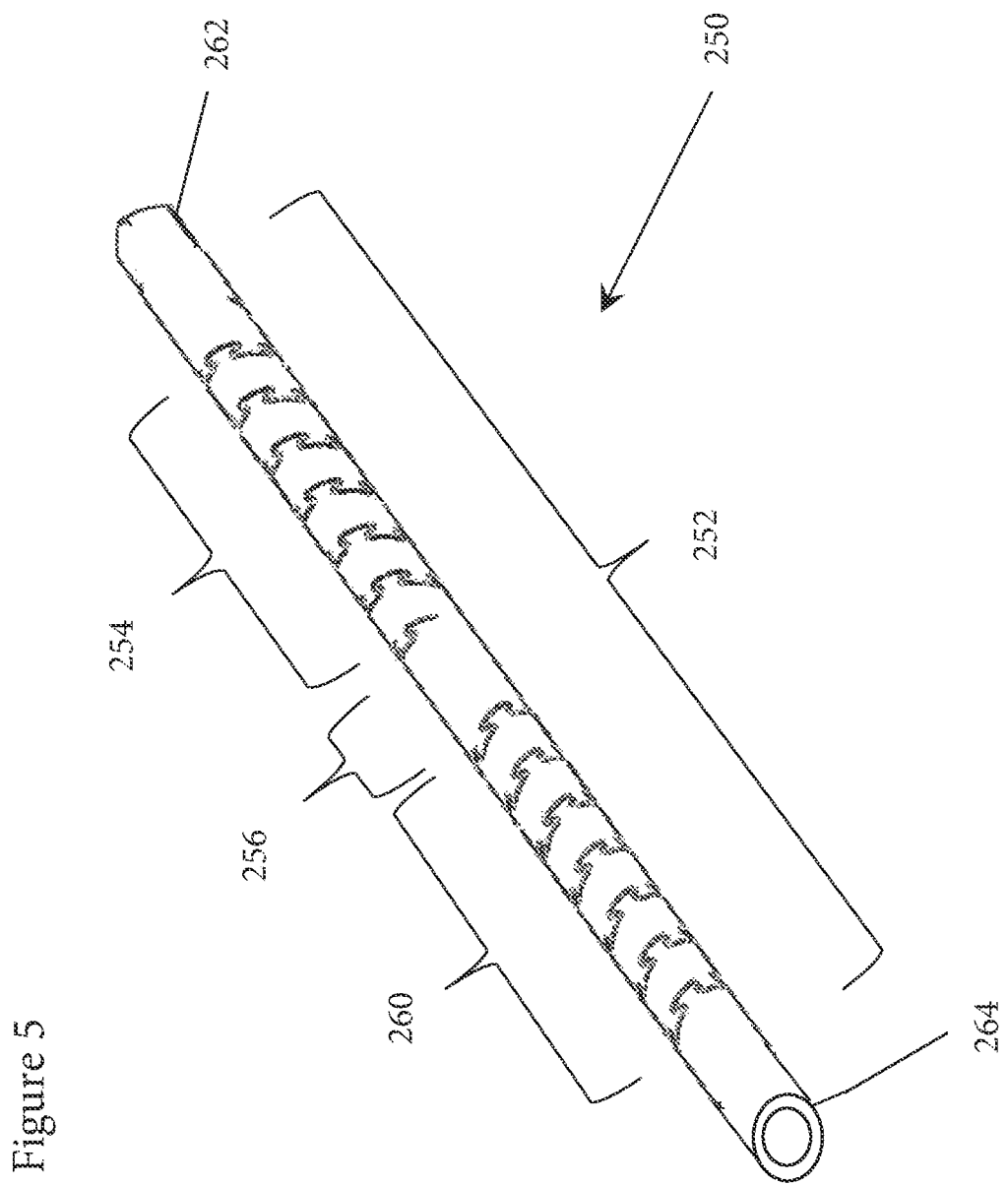
FIG. 5 is a perspective view of the disclosed flexible connection rod with two helical slots spaced by an inflexible section and un-tapered ends in accordance with the present invention.

In FIG. 5 the flexible connecting rod 250 contains two flexible areas 254 and flexible area 260 separated by an inflexible section 256. Flexible connecting rod 250 would be applicable for use in situations where connections need to be made in a U-shape and the length of the inflexible section 256 can be adjusted as required by end use. The connecting rod 250 can be inserted into the sleeves (not illustrated) to the point of commencement of the inflexible section 256, thereby leaving the inflexible section uncovered and the bend sharper. Alternatively, the sleeves (not illustrated) can abut one another as previously illustrated. The abutting of the sleeves would affect the bend between the inflexible section 256 and the flexible area 254 and flexible area 260, providing a softer bend.

As with the previously described flexible rods, the proximal end 262 and distal end 264 can be either open or closed, depending upon the use. When using the connecting rod 250 to secure and support a tube for the transport of fluid, the tube ends would require sealing. As with the prior designs, a proximal end 262 and distal end 264 are used to secure the connecting rod 250 within the structure through the use of applicable means.

Figure 6:
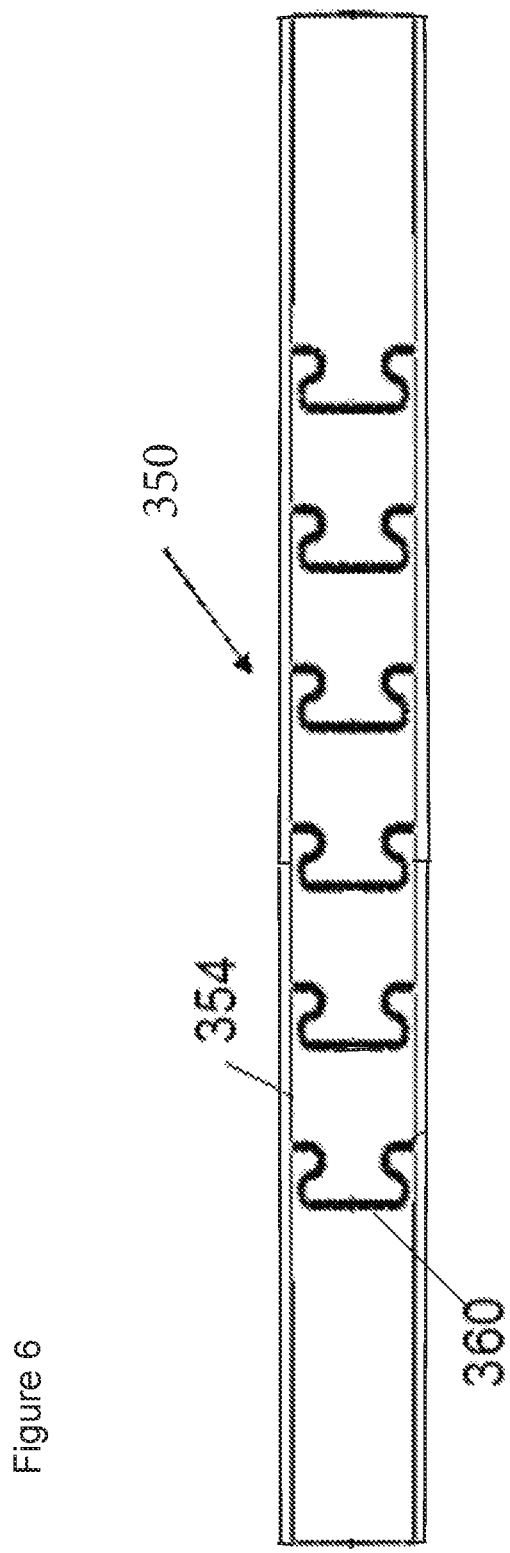
FIG. 6 is a perspective view of the disclosed flexible connection rod with circumferential slots and un-tapered ends in accordance with the present invention; 25)
Figure 7:
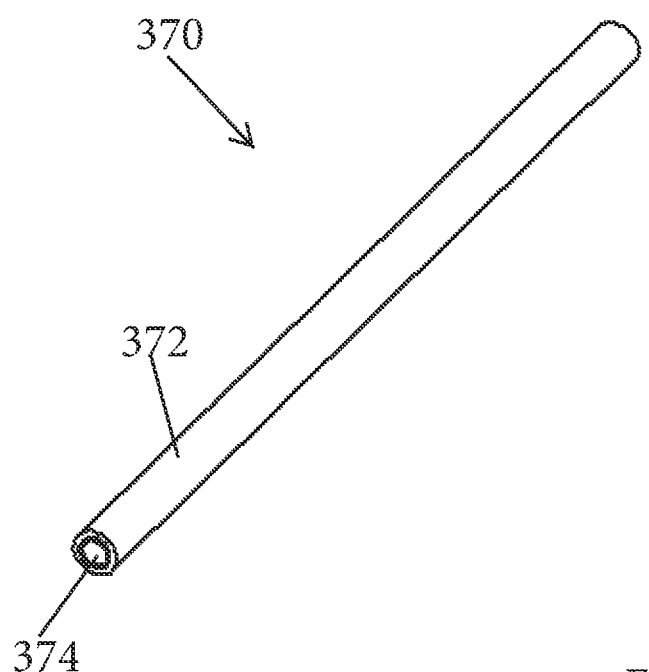
FIG. 7 is an isometric view of a flexible connection rod within a single sleeve in accordance with the present invention.

In the embodiment illustrated in FIG. 6, multiple concentric slots 360 are used to provide the flexibility of the flexible connecting rod 350. The flexible connecting rod 350 is illustrated covered by sleeve 354. Although the concentric slots 360 are illustrated in the central segment, the concentric slots 360 can extend to the ends of the connecting rod 350. As with the flexible connecting rod 250, the ends of the flexible connecting rod 350 can be tapered or straight, FIG. 7 illustrates a flexible connecting rod system 370 illustrated the connecting rod 374 within a full sleeve 372. The connecting rod 374 can be of any configuration disclosed herein. The full sleeve 372 can be substituted for the two sleeves illustrated heretofore and is advantageous, depending on the application.

Figure 9:
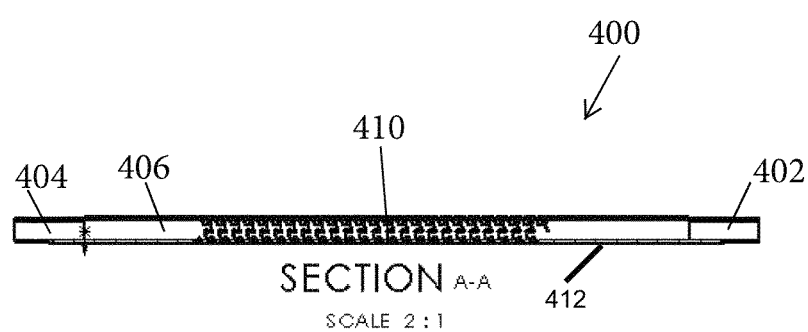
FIG. 9 is a sectional view of the flexible connection rod of FIG. 8 in accordance with the invention.
Figure 8:
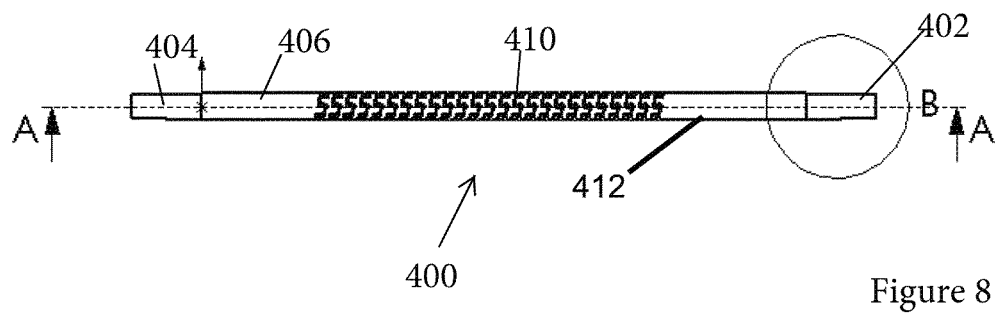
FIG. 8 is a plan view of a flexible connection rod having slightly tapered ends in accordance with the invention.

FIGS. 8 and 9 illustrate the flexible connecting rod system 400 with the flexible connecting rod 406, using a single slot 410 in a helical path, inserted into a clear sleeve 412. To facilitate insertion into the sleeve 412, each of the proximal end 402 and distal end 404 are tapered to some degree. The degree of taper would depend upon the application and both the distal end 404 and the proximal end 402 do not have to be tapered to the same degree. Nor do both ends require tapering as only one end can be tapered while the other maintains the same diameter as the body of the connecting rod 406. In this example the connecting rod 406 has open distal end 404 and proximal end 402, although they could be closed to meet end use needs.

Figure 10:
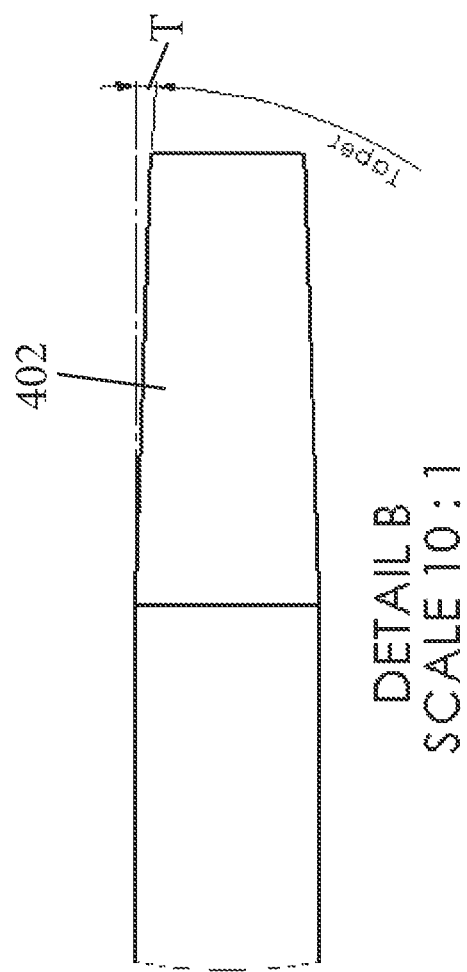
FIG. 10 is a detailed view of the taper of FIGS. 8 and 9 in accordance with the invention.

FIG. 10 shows in detail the taper T of the proximal end 402 of FIGS. 8 and 9. Although only the proximal end 402 is illustrated, the distal end 404 can be tapered to the same or greater degree or have no taper.

The tapers on the ends of the flexible connecting rod can be as high as 10-degrees to 15-degrees although more likely in the 5-degree to 10-degree range.

FIGS. 11 and 12 illustrate and example of a flexible connecting rod 452 having a closed end 456. The closed end can be used on the tapered and non-tapered rods, depending upon end use.

Although the sleeve 406 illustrated is a single, full sleeve, two sleeves as illustrated heretofore, can also be used. Additionally, the single slot 410 following the helical path can be replaced with the multiple concentric slots illustrated in FIG. 6.

As an alternative, one end of a rod can be fitted with a male connection while the other end fitted with a compatible female connection. This would enable the flexible connecting rods to be extended without the need to manufacture multiple longer sizes. Multiple sleeves can be used to cover the additional distance. Other means for connecting multiple connecting rods can be used and will be known to those skilled in the art.

One of the uses for the disclosed flexible connecting rod is in medical for the repair of bones. Examples of medical uses are disclosed and illustrated in FIGS. 9-11 of co-pending U.S. Ser. No. 16/155,362.

Any of the segments of the flexible rod can be either non-flexible or can be made flexible by the incorporation of a slot with a serpentine path along a helical or concentric path, or combination thereof, within the segment.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g.," which means "for example."

While in the foregoing we have disclosed embodiments of the invention in considerable detail, it will understood by those skilled in the art that many of these details may be varied without departing from the spirit and scope of the invention.

What is claimed is:

1. A flexible connecting system for the connection of structures, comprising:
   at least one flexible connecting rod, each of the at least one flexible connecting rod comprising:
      a body having an exterior diameter;
      a hollow interior core;
      a leading segment having an exterior diameter;
      a trailing segment having an exterior diameter;
      at least one slot following a sinuous, serpentine path to form a plurality of interlocking teeth, each of said at least one slot having a predetermined configuration; and
   at least one flexible sleeve, said at least one flexible sleeve comprising:
      a proximal end;
      a distal end;
      a hollow interior dimensioned to receive said at least one flexible connecting rod;
      an exterior; and
      at least one securing means securing each of the at least one flexible sleeve to the at least one flexible connecting rod, said at least one securing means configured to prevent movement of each of the at least one flexible sleeve along the at least one flexible connecting rod;
   wherein said at least one flexible sleeve covers at least a portion of the at least one flexible connecting rod with each of the at least one slot of the at least one flexible connecting rod being unfilled by the at least one flexible sleeve;
   wherein said at least one flexible sleeve prevents passage of material between the hollow interior core of said at least one flexible connecting rod and said exterior of said at least one flexible sleeve.

2. The flexible connecting system of claim 1 wherein said exterior diameter of said leading segment of the at least one flexible connecting rod and said exterior diameter of said trailing segment of the at least one flexible connecting rod have a diameter equal to said exterior diameter of said body.

3. The flexible connecting system of claim 1 wherein at least one of said leading segment of the at least one flexible connecting rod and said trailing segment of the at least one connecting rod has an open end to permit fluid flow.

4. The flexible connecting system of claim 3 wherein said fluid is a hardening material that anchors said at least one flexible connecting rod.

5. The flexible connecting system of claim 2 wherein said leading segment of the at least one flexible connecting rod and said trailing segment of the at least one connecting rod have closed ends.

6. The flexible connecting system of claim 1 wherein said exterior diameter of said leading segment of the at least one connecting rod and said exterior diameter of said trailing segment of the at least one flexible connecting rod are tapered.

7. The flexible connecting system of claim 6 wherein at least one of said leading segment of the at least one flexible connecting rod and said trailing segment of the at least one connecting rod has an open end to permit fluid flow.

8. The flexible connecting system of claim 6 wherein said fluid is a hardening material that anchors said at least one flexible connecting rod.

9. The flexible connecting system of claim 6 wherein at least one of said leading segment of the at least one flexible connecting rod and said trailing segment of the at least one connecting rod have closed ends.

10. The flexible connecting system of claim 1 wherein said at least one slot is a single slot in a helical pattern.

11. The flexible connecting system of claim 1 wherein the proximal end of one of the at least one slot is spaced from the distal end of a subsequent slot leaving an unslotted section.

12. The flexible connecting system of claim 1 wherein said at least one slot is multiple concentric slots.

13. The flexible connecting system of claim 1 wherein at least one of said proximal end and said distal end of said at least one flexible sleeve is open.

14. The flexible connecting system of claim 1 wherein at least one of said proximal end and said distal end of said at least one flexible sleeve is closed.

15. The flexible connecting system of claim 1 wherein said proximal end and said distal end of said at least one flexible sleeve are open and wherein said leading segment of the at least one flexible connecting rod and said trailing segment of the at least one connecting rod have open ends to enable fluid flow through said hollow interior of said at least one flexible connecting rod.

16. A method of surrounding a flexible connection rod in an impermeable configuration comprising the steps of:
 a) providing at least one flexible sleeve having a proximal end, distal end, and hollow body with dimensions for receiving said flexible connection rod, said flexible connection rod comprising:
  i) a body having an exterior diameter;
  ii) a hollow interior core;
  iii) a leading segment having an exterior diameter;
  iv) a trailing segment having an exterior diameter; and
  v) at least one slot following a sinuous, serpentine path to form a plurality of interlocking teeth, each of said at least one slot having a predetermined configuration;
 b) inserting said leading segment of said flexible connection rod into said distal end of said at least one flexible sleeve;
 c) manipulating said flexible connection rod within said at least one flexible sleeve to a position covering at least a portion of said at least one slot; and
 d) securing said flexible connection rod within said at least one flexible sleeve to prevent movement of said at least one flexible sleeve along said flexible connection rod;
 wherein inserting said flexible connection rod within said at least one flexible sleeve prevents the passage of material through said at least one slot of said flexible connecting rod covered by said at least one flexible sleeve.

17. The method of claim 16 wherein manipulating said flexible connection rod within said at least one flexible sleeve to a position covering at least a portion of said at least one slot further comprises a position covering all of said at least one slot on said flexible connection rod.

18. The method of claim 16 further comprising inserting said trailing segment of said flexible connection rod into said distal end of a second of said at least one flexible sleeve.

19. The method of claim 16 where said distal end of a first of said at least one flexible sleeve and said distal end of a second of said at least one flexible sleeve abut one another.

20. The method of claim 16 wherein at least one of said leading segment and said trailing segment of said flexible connection rod and at least one of said proximal end and said distal end of said at least one flexible sleeve is open to allow fluid flow into the core of said flexible connection rod.

* * * * *